United States Patent
Chen et al.

(10) Patent No.: US 6,303,536 B1
(45) Date of Patent: *Oct. 16, 2001

(54) PROCESS OF PREPARING CATALYST FOR PRODUCING ALKENYL ACETATES

(75) Inventors: Shien-Chang Chen, Taiwan; Fu-Shen Lin, Kaohsiung; Yuh-Lih Jong, Kaohsiung; Pi-Fwu Jang, Kaohsiung, all of (TW)

(73) Assignee: Dairen Chemical Coorporation, Taipei (TW)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/374,662

(22) Filed: Aug. 16, 1999

Related U.S. Application Data

(63) Continuation-in-part of application No. 09/165,340, filed on Oct. 2, 1998, now abandoned.

(30) Foreign Application Priority Data

Jun. 2, 1998 (TW) .................................................. 87108572

(51) Int. Cl.⁷ ............................. B01J 23/00; B01J 23/58; B01J 23/72; B01J 21/18; C07C 67/05
(52) U.S. Cl. ...................... 502/325; 502/328; 502/330; 502/331; 502/332; 502/333; 502/339; 502/340; 502/344; 502/345; 502/178; 502/183; 502/184; 502/185; 502/243; 502/244; 502/245; 502/251; 502/252; 502/253; 502/255; 502/262; 560/243; 560/245
(58) Field of Search ............................ 502/178, 183–185, 502/243–245, 251–253, 255, 262, 305, 306, 313, 317, 321, 328, 330, 331, 339, 340, 344, 345; 560/243, 245

(56) References Cited

U.S. PATENT DOCUMENTS

| | | | |
|---|---|---|---|
| 3,725,680 | 4/1973 | Silva | 307/268 |
| 3,743,607 | 7/1973 | Sennewald et al. | 252/430 |
| 3,775,342 | 11/1973 | Kronig et al. | 252/430 |
| 3,822,308 | 7/1974 | Kronig et al. | 260/497 A |
| 3,855,280 | 12/1974 | Severs, Jr. | 260/497 |
| 3,917,676 | 11/1975 | Kisaki et al. | 260/497 A |
| 3,939,199 | 2/1976 | Fernholz et al. | 260/469 |
| 3,960,934 | 6/1976 | Gaenzler et al. | 260/484 R |
| 4,013,712 | 3/1977 | Ragoonanan et al. | 260/497 R |
| 4,048,096 | 9/1977 | Bissot | 252/430 |
| 4,087,622 | 5/1978 | Nakamura et al. | 560/245 |
| 4,093,559 | 6/1978 | Fernholz et al. | 252/443 |
| 4,189,600 | 2/1980 | Weitz et al. | 560/246 |
| 4,450,290 | 5/1984 | Sanderson et al. | 560/246 |
| 4,668,819 | 5/1987 | Fernholz et al. | 560/245 |
| 4,732,883 | 3/1988 | Lyons et al. | 502/170 |
| 4,764,498 | 8/1988 | Wissner et al. | 502/251 |
| 5,179,056 | 1/1993 | Bartley | 502/170 |
| 5,250,487 | 10/1993 | Wirtz et al. | 502/243 |
| 5,536,693 | 7/1996 | Lemanski et al. | 502/300 |
| 5,567,839 | 10/1996 | Gulliver et al. | 560/245 |
| 5,808,136 | 9/1998 | Tacke et al. | 560/243 |

FOREIGN PATENT DOCUMENTS

| | | | |
|---|---|---|---|
| 0 361 484 | 9/1989 | (EP) . | |
| 0 519 435 | 6/1992 | (EP) . | |
| 1521652 | 8/1978 | (GB) | B01J/23/52 |

*Primary Examiner*—Mark L. Bell
*Assistant Examiner*—Patricia L. Hailey
(74) *Attorney, Agent, or Firm*—Jenkens & Gilchrist

(57) ABSTRACT

This invention relates to a preparation process of a catalyst which comprises a noble metal and a metal as catalysis promoter in combination with an alkali or alkaline earth metal compound, supported on the outer surface of a carrier. The preparation process comprises impregnating the carrier with a solution containing an oxidative state noble metal as the main catalyst and an oxidative state metal as catalysis promoter, reducing the oxidative state metals into the metallic state in gaseous phase with a gaseous reducing agent under certain temperature, pressure, moisture and gas concentration, then impregnating the reduced carrier with a solution of an alkali or alkaline earth metal compound. The metal components-supporting catalyst prepared by the process according to the present invention has a high surface area and exhibits high catalytic activity, which leads to increase the catalytic efficiency and life of this heterogeneous catalyst. The catalyst prepared in the present invention is suitable for producing alkenyl acetates through reaction of olefins, acetic acid and oxygen in vapor phase.

6 Claims, No Drawings

PROCESS OF PREPARING CATALYST FOR PRODUCING ALKENYL ACETATES

This application is a continuation-in-part application of application Ser. No. 09/165,340, filed Oct. 2, 1998, now abandoned.

FIELD OF THE INVENTION

This invention relates to a preparation process of a catalyst comprising noble metals as main component and other metals as catalysis promoter in combination with an alkali or alkaline earth metal compound, supported on the outer surface of a carrier, and also relates to use of a catalyst prepared according to the process of the present invention, for producing alkenyl acetates through reaction of olefins, acetic acid and oxygen in vapor phase.

BACKGROUND OF THE INVENTION

The industrial production of alkenyl acetates through reaction of olefins, oxygen and acetic acid in vapor phase has been performed in the presence of a heterogeneous catalyst, which comprises noble metals, metals as catalysis promoter in combination with an alkali or alkaline earth metal compound supported on the outer surface of a carrier. This preparation process has been known for a long time and the key point of this process, the evenly distribution of metal components on the surface of a supporting catalyst to provide high yield, also has been widely discussed and studied, mostly based on changing the kind or relative composition of the metal components. However, no matter how the metal composition or its structure has changed, the basic structure of all catalysts for producing alkenyl acetates is essentially a spherical shape catalyst prepared by impregnating on a carrier with the palladium metal, a metal for promoting catalysis, and an alkali or alkaline earth metal compound, wherein the metal for promoting catalysis is preferably gold and copper, and wherein the alkali or alkaline earth metal compound is preferably a potassium compound (U.S. Pat. No. 3,939,199, EP 0361484 and U.S. Pat. No. 4,668,819).

Earlier, the catalyst employed to produce vinyl acetate was prepared by impregnating palladium, gold and the like noble metals on the whole carrier (U.S. Pat. Nos. 3,725,680, 3,743,607); the catalyst employed to produce allyl acetate was prepared by impregnating palladium, copper and the like noble metals on the whole carrier (U.S. Pat. No. 3,917,676). That is, the active noble metals were supported on the interiors and outer surface of a carrier. However, while the catalyst was prepared in this way, it was found in actual reaction that the reactants were scarcely able to efficiently diffuse into inner regions of the carrier, so that the interior active palladium and gold or copper metals were not able to be sufficiently utilized. In order to improve this drawback, in the preparation process of the catalyst for producing alkenyl acetates, usually, instead of impregnating palladium metal and a metal for promoting catalysis on the whole carrier, but to evenly impregnate on the surface of a carrier. That is, to impregnate palladium metal and the metal for promoting catalysis evenly on the surface layer of a carrier to form a spherical shape supported catalyst (U.S. Pat. No. 4,087,622). The preparation method was that the carrier was impregnated with the active metallic materials first, then these metal salts were precipitated by immersing in a solution containing an alkali or alkaline earth metal salts (U.S. Pat. No. 4,048,096, U.S. Pat. No. 3,775,342).

Further, it was known that when preparing the catalyst with palladium and other metals as catalysis promoter in combination with an alkali or alkaline earth metal compound, a special carrier was used. This carrier was washed with acids before the impregnation and treated with bases after the impregnation (EP-A-0519435).

Since palladium and the metal for promoting catalysis were non-homogeneous during the impregnation, which would result in the non-homogenous distribution on the surface of a carrier, therefore, many researches have been made on this problem (U.S. Pat. No. 4,087,622, U.S. Pat. No. 3,822,308 and British Patent 1521652). As a result, in the preparation of the catalyst for producing alkenyl acetates, the catalyst was essentially prepared by impregnating palladium and a metal for promoting catalysis, in combination with an alkali or alkaline earth metal compound on the surface of a spherical shape carrier. The preparation process generally was comprised of the following steps: (1) a carrier was impregnated with an aqueous solution of soluble palladium ions and metal ions for promoting catalysis; (2) the impregnated carrier was immersed in an alkali solution, so that the soluble palladium ions and metal ions for promoting catalysis were precipitated on the surface layer of the carrier and formed into insoluble oxidative state palladium and metal for promoting catalysis; (3) the treated carrier was washed with water to remove soluble ions produced during the precipitation; (4) the oxidative state palladium and metal for promoting catalysis supported on the treated carrier were then reduced to the metallic state; (5) the reduced carrier in (4) was impregnated with a solution of an alkali or alkaline earth metal compound; and (6) the impregnated carrier in (5) was dried. Among these steps, conventionally, the reducing step (4) was performed by a reducing process using liquid reducing agents in liquid phase. However, since non-homogenous nature of palladium and the metal as catalysis promoter on the surface of the carrier, the catalyst prepared by this method is usually unsatisfactory.

In order to resolve the above problem, in the preparation process of the catalyst for producing alkenyl acetates according to the present invention, the conventional reducing process utilizing liquid reducing agents in liquid phase is changed into a reducing process utilizing gaseous reducing agents in gaseous phase. As a result, the catalyst comprising palladium and a metal as catalysis promoter in combination with an alkali and alkaline earth metal compound supported on a carrier prepared by using this present invention has a high metal surface area and exhibits high catalytic activity, thus the catalytic efficiency and life of this heterogeneous catalyst are improved.

SUMMARY OF THE INVENTION

This invention relates to a preparation process of a catalyst which comprises a noble metal and a metal as catalysis promoter in combination with an alkali or alkaline earth metal compound, supported on the outer surface of a carrier. The preparation process comprises impregnating the carrier with a solution containing an oxidative state noble metal as the main catalyst and an oxidative state metal as catalysis promoter, reducing the oxidative state metals into the metallic state in gaseous phase with a gaseous reducing agent under certain temperature, pressure, moisture and gas concentration, then impregnating the reduced carrier with a solution of an alkali or alkaline earth metal compound. The metal components-supporting catalyst prepared by the process according to the present invention has a high surface area and exhibits high catalytic activity, which leads to increase the catalytic efficiency and life of this heterogeneous catalyst. The catalyst prepared in the present invention is suitable for producing alkenyl acetates through reaction of olefins, acetic acid and oxygen in vapor phase.

DETAILED DESCRIPTION OF THE INVENTION

This invention relates to a preparation process of a catalyst which comprises a noble metal as main component and other metals as catalysis promoter in combination with an alkali or alkaline earth metal compound, all of which are supported on the outer surface of a carrier. The examples of the suitable carrier are alumina, silica gel, silica, active carbon, silicon carbide, diatomaceous earth, pumice and the like, while among them silica is preferable. The example of the noble metal is palladium; the examples of the metal as catalysis promoter are gold, copper, molybdenum, cadmium and magnesium, while among them gold and copper are preferable. The examples of the alkali or alkaline earth metal compounds are the hydroxides, acetates, nitrates and bicarbonates of potassium, sodium, cesium, magnesium, barium and the like, while among them potassium salts are preferable, and potassium acetate is even more preferable.

The distinctive feature of the process according to the present invention is, in preparing the catalyst for producing alkenyl acetates, the conventional reducing process utilizing liquid reducing agents in liquid phase is changed into a reducing process utilizing gaseous reducing agents in gaseous phase to carry out the reduction of the oxidative state metals. After treatment with an alkali solution to transform the oxidative state noble metal and metal for promoting catalysis (which are supported on the carrier after the impregnation) into hydroxide state, these are reduced with suitable gaseous reducing agents in specific reductive conditions and transformed into the metallic state.

The term "oxidative state" used herein according to the present invention means a metal in cationic state, for example, oxidative state palladium means $Pd^{2+}$.

In the preparation process according to the present invention, after the metal components are supported on the surface layer of a carrier by means of conventionally well-known method, the heretofore un-reduced catalyst is placed in a reactor, and a gaseous reducing agent is used under suitable reducing conditions in gaseous phase to reduce the oxidative state metals into metallic state metals. While the examples of gaseous reducing agents used in the present invention are hydrogen and ethylene, hydrogen is preferable. In the reducing process, it is preferable to dilute the gaseous reducing agent with inert gas (such as nitrogen gas). The volume percentage of the reducing agent after dilution is in the range of 0.05 to 75%, and preferably, 5 to 30%. The amount of the reducing agent used depends on the amounts of the noble metal, the metal for promoting catalysis and the moisture content of the reducing conditions, the equivalents used thereof usually should be at least 1 to 1.5 times of the equivalents required to reduce the catalyst; if necessary, more reducing agents can be used. The reducing temperature is usually between 100 to 300° C., and preferably, between 150 to 250° C. The reducing pressure is usually between 0 to 5 kg/cm² (gauge pressure), and preferably, between 1.5 to 3.5 kg/cm² (gauge pressure). The moisture content is controlled below 5000 ppm, and preferably, in the range of 50 to 2000 ppm.

After the reducing process, the reduced catalyst is washed with deionized water until the chloride ions are completely removed and then dried. After drying, it is impregnated with an aqueous solution containing an alkali or alkaline earth metal compound. Finally, the catalyst is dried at a temperature between 80 to 150° C. until the water content is between 0 to 6% by weight, and preferably, 1 to 3% by weight.

The metal components-supporting catalyst prepared in the present invention is suitable for producing alkenyl acetates through reaction of olefins, acetic acid and oxygen in vapor phase. Said olefinic compounds include ethylene, propylene, isobutylene and the like. For example, the catalyst prepared in the present invention can be used in the presence of ethylene, acetic acid and oxygen in vapor phase to produce vinyl acetate. The catalyst employed in this producing process comprises palladium, gold and an alkali or alkaline earth metal compound (a potassium compound is preferred). Also, the catalyst prepared in the present invention may be used in the presence of propylene, acetic acid and oxygen in vapor phase to produce allyl acetate. The catalyst employed in this producing process comprises palladium, copper (barium and lead can further be added), and an alkali or alkaline earth metal compound (a potassium compound is preferred).

A certain amount of the above prepared catalyst for producing alkenyl acetates is placed in a reacting tube with an inner diameter of 20mm and a length of 2.0 m. Under a specific pressure at the inlet of the reacting tube, the reacting gases are introduced into the tube at a reacting temperature set according to the activity of the catalyst. These reacting gases comprises 30 to 45 volume % of olefin, 30 to 50 volume % of nitrogen gas, 5 to 15 volume % of acetic acid and 3 to 7 volume % of oxygen. The yield of alkenyl acetate is determined by analyzing the composition at the exit of the tube in a definite time.

Generally, the selection of a catalyst in the industry is based on the catalytic activity. The catalytic activity can be calculated basically according to the following formula:

The activity of a catalyst:

$$STY(\text{space time yield}) = \frac{\text{weight of alkenyl acetates produced (g)}}{\text{volume(I) of catalyst} \times \text{sampling time (hr)}}$$

The selectivity of a catalyst:

$$C2 \text{ selectivity} = \frac{\text{moles of vinyl acetate produced}}{\text{moles of vinyl acetate produced} + 1/2 \text{ moles of } CO_2 \text{ produced}}$$

$$C3 \text{ selectivity} = \frac{\text{moles of allyl acetate produced}}{\text{moles of allyl acetate produced} + 1/3 \text{ moles of } CO_2 \text{ produced}}$$

As the surface area of metals in the catalyst prepared according to the present invention is higher compared to those of the catalyst prepared by the reducing process using liquid reducing agents, so is the efficiency of the catalyst in the present invention higher. It is confirmed from the evaluation of the catalytic activity that when the catalyst is used to produce alkenyl acetates, the catalyst prepared in the present invention not only provides higher activity of the whole reaction of olefins, acetic acid and oxygen, but also prolongs its own life. That is, compared to the conventional catalyst, the catalyst of the present invention is able to yield more alkenyl acetates per unit volume of catalyst in the reactor and per unit time when the conditions of the synthetic reaction (such as pressure, temperature, oxygen concentration) remain constant. Moreover, if the productive yield remains constant, not only the reacting temperature can be decreased, but also the selectivity of the reaction can be higher, which leads to less production of carbon dioxide and less product loss during removal of carbon dioxide, thus the unit raw material consumption will be lower.

The present invention will be further described with reference to the following Examples and Comparative Examples, but the scope of the present invention is by no means limited.

EXAMPLE 1

The carrier employed in this Example was a porous carrier of alumina/silica with an outer diameter of 5 mm and was available from SUD-CHEMIE AG. This carrier had a surface area of 100 to 120 m2/g, a pore volume of 0.7 to 0.9 ml/g and a bulk density of 600 g/l. The metal component-supporting catalyst was prepared according to the following steps:

Step 1): An aqueous $Na_2PdCl_4$ solution with weight of 2.2 kg containing 15 weight % of palladium was added into an aqueous $HAuCl_4$ solution with weight of 0.5 kg containing 30 weight % of gold. The mixture was then diluted with deionized water till total volume was 37.2 l. 100 l of alumina/silica carrier was placed in an impregnating tank with rotation rate of 24 turns per minute. The mixture was added rapidly in 10 minutes.

Step 2): Hot air was passed through to dry the carrier until the remained moisture was less than 4%. The temperature of the hot air was lower than 120° C.

Step 3): 28 weight % NaOH solution with weight of 160% the amount absorbed by the carrier (about 60 kg) was added to the dried catalyst. The immersing time was over 20 hours. The originally soluble chloride state palladium and gold were transformed into insoluble hydroxide state palladium and gold.

Step 4): The impregnated catalyst carrier after drying was placed in a reducing reactor with temperature controlled at 165° C. and pressure set at 2 kg/cm² (gauge pressure). The reducing gases were passed into the reactor with a flow rate of 15 cm/sec, wherein the composition of the reducing gases was hydrogen:nitrogen=1:3. The moisture content of the reducing condition was controlled below 2000 ppm. The hydroxide state palladium and gold were reduced into metallic state palladium and gold.

Step 5): The above catalyst was washed to remove chloride ions with the amount of 15 to 16 liters of deionized water per liter of the catalyst until the catalyst was free of chloride ions.

Step 6): The catalyst carrier was dried as in step 2).

Step 7): An adequate amount of potassium acetate was added into the dried catalyst carrier, so that each liter of the catalyst contained 30 g weight of potassium acetate.

Step 8): The catalyst carrier was dried as in step 2).

After the above steps, a catalyst contained 3.3 g/l of palladium, 1.5 g/l of gold and 30 g/l of potassium acetate was obtained, wherein all palladium and gold were well distributed on the surface of the carrier and the surface area of metals was determined, the results are listed in Table 1.

Nine hundred milliliters of the catalyst thus obtained was charged into a reacting tube with an inner diameter of 20 mm and a length of 2.0 m. Under a pressure of 8 kg/cm² (gauge pressure) at the inlet of the reactor, the reacting gaseous mixture was introduced into the reactor at a temperature of 140° C. The gaseous mixture was comprised of 41 volume % of ethylene, 43 volume % of nitrogen gas, 10 volume % of acetic acid and 6 volume % of oxygen. While the composition at the exit was analyzed in a definite time, the activity and the selectivity of the catalyst were calculated. The results are listed in Table 1.

When the activity and the selectivity of the catalyst were evaluated, the crude product at the exit of the reactor was cooled with chilled water, and the composition was analyzed by Shimadzu Gas Chromatography. The flow rate of the gases was determined by Shinagawa Dry Gas Meter and the surface area of metals was determined according to Chemi-Sorp Method as in ASTM D3908.

EXAMPLE 2

This is a repetition of Example 1 except that, an aqueous $Na_2PdCl_4$ solution with weight of 2.2 kg containing 18 weight % of palladium and an aqueous $HAuCl_4$ solution with weight of 0.5 kg containing 36 weight % of gold were prepared. As well, a catalyst was obtained that contained 4.0 g/l of palladium, 1.8 g/l of gold and 30 g/l of potassium acetate, wherein all palladium and gold were well distributed on the surface of the carrier.

This catalyst was evaluated by the same methods as in Example 1, and the results are listed in Table 1.

EXAMPLE 3

This is a repetition of Example 1 except that, an aqueous $Na_2PdCl_4$ solution with weight of 2.2 kg containing 22.5 weight % of palladium and an aqueous HAuCl4 solution with weight of 0.5 kg containing 45 weight % of gold were prepared. As well, a catalyst was obtained that contained 5.0 g/l of palladium, 2.25 g/l of gold and 30 g/l of potassium acetate, wherein all palladium and gold were well distributed on the surface of the carrier.

This catalyst was evaluated by the same methods as in Example 1, and the results are listed in Table 1.

EXAMPLE 4

This is a repetition of Example 1 except that, an aqueous $Na_2PdCl_4$ solution with weight of 2.2 kg containing 30 weight % of palladium and an aqueous $HAuCl_4$ solution with weight of 0.5 kg containing 60 weight % of gold were prepared. As well, a catalyst was obtained that contained 6.6 g/l of palladium, 3.0 g/l of gold and 30 g/l of potassium acetate, wherein all palladium and gold were well distributed on the surface of the carrier.

This catalyst was evaluated by the same methods as in Example 1, and the results are listed in Table 1.

Comparative Example 1

This is a repetition of Example 1, wherein the catalyst was prepared with an aqueous $Na_2PdCl_4$ solution with weight of 2.2 kg containing 15 weight % of palladium and an aqueous $HAuCl_4$ solution with weight of 0.5 kg containing 30 weight % of gold except that step 4) was altered as follows: the impregnated 5 mm porous carrier after step 3) was poured into 50 l of an aqueous solution containing 5% $N_2H_4$ for 4 hours, so that the hydroxide state palladium and gold deposited on the carrier were reduced into metallic state palladium and gold. The same procedures thereafter as in Example 1 were followed, and the carrier was washed, potassium acetate was added and the catalyst carrier was dried.

This catalyst was evaluated by the same methods as in Example 1, and the results are listed in Table 1.

Comparative Example 2

This is a repetition of catalyst preparation as in Comparative Example 1 except that an aqueous $Na_2PdCl_4$ solution with weight of 2.2 kg containing 18 weight % of palladium and an aqueous $HAuCl_4$ solution with weight of 0.5 kg containing 36 weight % of gold were prepared.

This catalyst was evaluated by the same methods as in Example 1, and the results are listed in Table 1.

Comparative Example 3

This is a repetition of catalyst preparation as in Comparative Example 1 except that an aqueous $Na_2PdCl_4$ solution with weight of 2.2 kg containing 22.5 weight % of palladium and an aqueous $HAuCl_4$ solution with weight of 0.5 kg containing 45 weight % of gold were prepared.

This catalyst was evaluated by the same methods as in Example 1, and the results are listed in Table 1.

Comparative Example 4

This is a repetition of catalyst preparation as in Comparative Example 1 except that an aqueous $Na_2PdCl_4$ solution with weight of 2.2 kg containing 30 weight % of palladium and an aqueous $HAuCl_4$ solution with weight of 0.5 kg containing 60 weight % of gold were prepared.

This catalyst was evaluated by the same methods as in Example 1, and the results are listed in Table 1.

Comparative Example 5

This is a repetition of Example 1 except that, the moisture content of the reducing condition in Example 1 was not controlled and was above 2000 ppm. As well, in Comparative Example 5, a catalyst was obtained that contained 3.3 g/l of palladium, 1.5 g/l of gold and 30 g/l of potassium acetate, wherein all palladium and gold were well distributed on the surface of the carrier.

This catalyst was evaluated by the same methods as in Example 1, and the results are listed in Table 1.

EXAMPLE 5

This is a repetition of catalyst preparation as in Example 1 except that $Na_2PdCl_4$ solution with weight of 2.2 kg containing 15 weight % of palladium and an aqueous $CuCl_2$ solution with weight of 0.5 kg containing 14.6 weight % of copper were prepared.

After the above steps, a catalyst was obtained that contained 3.3 g/l of palladium, 0.34 g/l of copper and 30 g/l of potassium acetate, wherein all palladium and copper were well distributed on the surface of the carrier.

Six hundred milliliters of thus obtained catalyst was charged into a reacting tube with an inner diameter of 20 mm and a length of 2.0 m. Under a pressure of 7.0 kg/cm2 (gauge pressure) at the inlet of the reactor, the reacting gaseous mixture was introduced into the reactor at a temperature of 148° C. The gaseous mixture was comprised of 29 volume % of propylene, 44 volume % of nitrogen gas, 6.7 volume % of acetic acid 13.5 volume % of steam and 6.5 volume % of oxygen. According to the same methods as in Example 1, while the composition at the exit was analyzed in a definite time, the activity and the selectivity of the catalyst were calculated, and the surface area of metals was determined. The results ware listed in Table 1.

EXAMPLE 6

This is a repetition of catalyst preparation as in Example 1 except that an aqueous $Na_2PdCl_4$ solution with weight of 2.2 kg containing 15 weight % of palladium and an aqueous $CuCl_2$ solution with weight of 0.5 kg containing 6.0 weight % of copper were prepared.

This catalyst was evaluated by the same methods as in Example 5, and the results are listed in Table 1.

EXAMPLE 7

This is a repetition of catalyst preparation as in Example 1 except that an aqueous $Na_2PdCl_4$ solution with weight of 2.2 kg containing 22.5 weight % of palladium and an aqueous $CuCl_2$ solution with weight of 0.5 kg containing 14.6 weight % of copper were prepared.

This catalyst was evaluated by the same methods as in Example 5, and the results are listed in Table 1.

Comparative Example 6

This is a repetition of catalyst preparation as in Comparative Example 1 except that an aqueous $Na_2PdCl_4$ solution with weight of 2.2 kg containing 15 weight % of palladium and an aqueous $CuCl_2$ solution with weight of 0.5 kg containing 14.6 weight % of copper were prepared.

This catalyst was evaluated by the same methods as in Example 5, and the results are listed in Table 1.

Comparative Example 7

This is a repetition of catalyst preparation as in Comparative Example 1 except that an aqueous $Na_2PdCl_4$ solution with weight of 2.2 kg containing 15 weight % of palladium and an aqueous $CuCl_2$ solution with weight of 0.5 kg containing 6.0 weight % of copper were prepared.

This catalyst was evaluated by the same methods as in Example 5, and the results are listed in Table 1.

Comparative Example 8

This is a repetition of catalyst preparation as in Comparative Example 1 except that an aqueous $Na_2PdCl_4$ solution with weight of 2.2 kg containing 22.5 weight % of palladium and an aqueous $CuCl_2$ solution with weight of 0.5 kg containing 14.6 weight % of copper were prepared.

This catalyst was evaluated by the same methods as in Example 5, and the results are listed in Table 1.

Comparative Example 9

This is a repetition of Example 1 except that instead of hydrogen, ethylene was used as the gaseous reducing agent in the reducing process.

This catalyst was evaluated by the same methods as in Example 1, and the results are listed in Table 1.

Comparative Example 10

This is a repetition of Example 5 except that, the moisture content of the reducing condition in Example 5 was not controlled and was above 2000 ppm. As well, in Comparative Example 10, a catalyst was obtained that contained 3.3 g/l of palladium, 0.34 g/l of copper and 30 g/l of potassium acetate, wherein all palladium and copper were well distributed on the surface of the carrier.

This catalyst was evaluated by the same methods as in Example 5, and the results are listed in Table 1.

TABLE 1

| | Activity (g/l/hr) | Selectivity (%) | Surface Area of Metals (m²/g. metal) |
|---|---|---|---|
| Example 1 | 401 | 95.4 | 138 |
| Example 2 | 456 | 95.7 | 143 |
| Example 3 | 632 | 94.8 | 123 |
| Example 4 | 785 | 95.4 | 117 |
| Comparative Example 1 | 327 | 95.5 | 123 |
| Comparative Example 2 | 380 | 95.6 | 122 |
| Comparative Example 3 | 440 | 94.1 | 102 |
| Comparative Example 4 | 537 | 92.6 | 101 |
| Comparative Example 5 | 365 | 94.3 | 118 |
| Example 5 | 609 | 97.5 | 120 |
| Example 6 | 554 | 97.0 | 127 |
| Example 7 | 689 | 97.3 | 125 |
| Comparative Example 6 | 547 | 96.4 | 105 |
| Comparative Example 7 | 497 | 96.0 | 109 |
| Comparative Example 8 | 612 | 96.7 | 109 |
| Comparative Example 9 | 306 | 96.2 | 101 |
| Comparative Example 10 | 502 | 95.5 | 98 |

What is claimed is:

1. A preparing process of a catalyst, which comprises (a) impregnating on the surface of a catalyst carrier with a solution containing an oxidative state noble metal as the main catalyst and an oxidative state metal as catalysis promoter, reducing the metals from an oxidative state into a metallic state in gaseous phase with a gaseous reducing agent at a moisture content of from 50 to 2000 ppm, and a temperature in the range of from 100 to 300° C., and a pressure in the range of from 0 to 5 kg/cm² (gauge pressure); and (b) impregnating the reduced catalyst with a solution of alkali or alkaline earth metal compound, then drying the catalyst.

2. The process according to claim 1, wherein said oxidative state noble metal is palladium.

3. The process according to claim 1, wherein said oxidative state metal as catalysis promoter is selected from the group consisting of gold, copper, molybdenum, cadmium and magnesium.

4. The process according to claim 1, wherein said alkali or alkaline earth metal compound is selected from the group consisting of hydroxides, acetates, nitrates and bicarbonates of potassium, sodium, cesium, magnesium and barium.

5. The process according to claim 1, wherein said catalyst carrier is selected from the group consisting of alumina, silica gel, silica, active carbon, silicon carbide, diatomaceous earth and pumice.

6. The process according to claim 1, wherein said gaseous reducing agent is hydrogen.

* * * * *